United States Patent
Zhang et al.

(10) Patent No.: US 11,452,777 B2
(45) Date of Patent: Sep. 27, 2022

(54) METHOD FOR SYNTHESIZING A NEW FERRIHYDRITE NANO-PHOTOSENSITIZER AND ITS ANTIBACTERIAL AND ANTICANCER USE

(71) Applicant: Northwestern Polytechnical University, Xi 'an (CN)

(72) Inventors: Lianbing Zhang, Xi 'an (CN); Yingchun Yang, Xi 'an (CN); Qing Tian, Xi 'an (CN); Aipeng Li, Xi 'an (CN); Yao Chen, Xi 'an (CN)

( * ) Notice: Subject to any disclaimer, the term of this patent is extended or adjusted under 35 U.S.C. 154(b) by 55 days.

(21) Appl. No.: 15/734,232

(22) PCT Filed: Dec. 20, 2019

(86) PCT No.: PCT/CN2019/126862
§ 371 (c)(1),
(2) Date: Dec. 2, 2020

(87) PCT Pub. No.: WO2021/047099
PCT Pub. Date: Mar. 18, 2021

(65) Prior Publication Data
US 2021/0260191 A1   Aug. 26, 2021

(30) Foreign Application Priority Data

Sep. 11, 2019 (CN) .......................... 201910858907.4

(51) Int. Cl.
*A61K 41/00* (2020.01)
*A61P 31/04* (2006.01)
*A61P 35/00* (2006.01)
*A61K 9/16* (2006.01)

(52) U.S. Cl.
CPC ........ *A61K 41/0057* (2013.01); *A61K 9/1641* (2013.01); *A61K 9/1694* (2013.01); *A61P 31/04* (2018.01); *A61P 35/00* (2018.01)

(58) Field of Classification Search
CPC .............. A61K 41/0057; A61K 9/1641; A61K 9/1694; A61K 47/60; A61K 47/6931; A61K 47/6923; A61P 31/04; A61P 35/00; B82Y 5/00; B82Y 40/00
See application file for complete search history.

(56) References Cited

PUBLICATIONS

Carta et al., Materials Chemistry and Physics 113 (2009) 349-355 (Year: 2009).*
Grigorie et al., Themochimica Acta 621 (2015) 61-67 (Year: 2015).*

* cited by examiner

*Primary Examiner* — Robert S Cabral (57) ABSTRACT

The present invention discloses a method for synthesizing a new ferrihydrite nano-photosensitizer, comprising steps of: weighing 303 mg of $Fe(NO_3)_3 \cdot 9H_2O$ solid dissolved fully in 30 ml of distilled water to prepare a 0.75 mM of $Fe(NO_3)_3$ solution in water; adding PEG solid to the solution in water by stirring to fully dissolve at a molar ratio of PEG to $Fe^{3+}$ of 1:1-1:50; stirring the obtained solution under heating at 75° C. in a water bath for 10-50 minutes, and then immediately cooling in an ice bath after removing; centrifuging and washing the cooled mixed solution at high speed under low temperature with the supernatant discarded, to obtain pellets as PEG-modified ferrihydrite nanoparticles (PEG-Fns). The PEG-Fns synthesized in the present invention can be controllably induced and reduced by blue light to release $Fe^{2+}$, and then produce •OH through Fenton reaction of $Fe^{2+}$ and $H_2O_2$ in the cell, which induces cell oxidative damage, thereby achieving controllable anticancer and antibacterial purposes.

6 Claims, 12 Drawing Sheets

METHOD FOR SYNTHESIZING A NEW FERRIHYDRITE NANO-PHOTOSENSITIZER AND ITS ANTIBACTERIAL AND ANTICANCER USE

TECHNICAL FIELD

The present invention belongs to the technical field of an antibacterial drug and an anticancer drug, particularly relates to a method for synthesizing a new ferrihydrite nano-photosensitizer and its antibacterial and anticancer use.

BACKGROUND

The increased level of reactive oxygen species (ROS) in cancer cells is an important way to achieve both symptoms and root causes of cancer. Currently, the increase of ROS in cancer cells is mainly achieved by inhibiting the antioxidant system through the intracellular pathway. It has been reported that small molecules (piplartine) can specifically increase the level of ROS in cancer cells, thereby selectively inducing cancer cell death, and having no effect on normal tissues and rapidly proliferating non-tumor cells (*Nature* 2011, 475, 231-234.). However, such methods have relatively limited anti-cancer effects and may cause a series of complications. For example, the production of a large amount of ROS which is a signal molecule in the live signaling pathway, will lead to an increased incidence of liver cirrhosis and type 2 diabetes. In addition, ultra-small silica and ferumoxytol have been reported to kill cancer cells by increasing intracellular ROS (*Nature Nanotechnology*, 2016, 11, 977-985. *Nature Nanotechnology*, 2016, 11, 986-994.), but such method has a serious drawback of not being able to achieve a controlled increase in ROS level in cancer cells.

Pathogenic microorganisms are widely present in the environment, with a wide range of species, rapid spread, and easy to cause adverse reactions in the body. Although traditional fungicides have good antibacterial and sterilization properties, they have problems such as short duration, large dosage, and their own or by-products that are harmful to the surrounding environment. Therefore, the research and development of a long-acting, stable, environmentally friendly fungicide and antibacterial material has become a focus for scholars. Although some research teams use the peroxidase activity of synthetic graphene quantum dots to catalyze •OH production for antibacterial treatment (*ACS Nano*, 2014, 8(6):6202-6210.), this method cannot be widely applied due to the shortage of expensive raw materials and complicated procedures. Therefore, it is necessary to develop a new and inexpensive antibacterial technology.

The most important ROS production pathway in cells of the body is the Fenton reaction ($Fe^{2+}+H_2O_2 \rightarrow Fe^{3+}+\cdot OH+OH^-$) between ferrous ion ($Fe^{2+}$) and $H_2O_2$ to produce an active free radical such as •OH, wherein •OH has a strong oxidizing ability and a short half-life, which is the freedom of greater toxicity. Therefore, the production of •OH induced by exogenous $Fe^{2+}$ can be used to kill cancer cells; in addition, in terms of antibacterial, •OH can induce bacterial and fungal death due to its long half-life, high toxicity and easy reaction with lipids of microbial cell membranes. In summary, •OH can play a role of clearance and inhibition in antibacterial and antitumor. Ferrihydrite is a widely-recognized photo-Fenton reaction catalyst, which can quickly reduce the trivalent iron to divalent iron and release it as free $Fe^{2+}$ out under the irradiation of light of ≤580 nm; and the released $Fe^{2+}$ could convert $H_2O_2$ into •OH through Fenton reaction. Therefore, the ferrihydrite-mediated photo-Fenton reaction has the potential to become a new antibacterial and anticancer approach.

Currently, synthetic ferrihydrite was mainly used to adsorb and degrade organic matters with its adsorption capacity and photo-Fenton activity, but there have been no reports about its use in the regulation of ROS level in organisms and antibacterial and antitumor activities. The reason thereof may be that the ferrihydrite synthesized by the existing method is in an agglomerated state, and its morphology and particle size cannot meet the requirement of pharmaceutical use (CN 108686624 A. *Physica B-Condensed Matter* 2017, 513, 58-61. *Materials Chemistry And Physics* 2009, 113, 349-355.). Therefore, it is necessary to synthesize a new type of ferrihydrite with good dispersibility, morphology and particle size through a new method and realize its effective use in antitumor and antibacterial.

SUMMARY OF THE INVENTION

The objective of the present invention is to overcome the above defects in cancer treatment, antibacterial and ferrihydrite nanoparticles synthesis technology and to meet clinical requirements, the present invention synthesizes a new type of photosensitive PEG-modified ferrihydrite nanoparticles (PEG-Fns) with small particle size and high dispersibility, which releases $Fe^{2+}$ under the action of blue light and the released $Fe^{2+}$ can convert $H_2O_2$ into •OH through Fenton reaction. Finally, an highly effective and controllable antibacterial and antitumor effects can be achieved.

In order to achieve the above objective, the first aspect of the present invention provides a method for synthesizing a new ferrihydrite nano-photosensitizer, comprising steps of:
(1) weighing 303 mg of $Fe(NO_3)_3 \cdot 9H_2O$ solid dissolved fully in 30 ml of distilled water to prepare a 0.75 mM of $Fe(NO_3)_3$ solution in water;
(2) adding PEG solid as a modifier to the solution in water obtained in step (1) by stirring to fully dissolve at a molar ratio of PEG to $Fe^{3+}$ of 1:1-1:50;
(3) stirring the solution obtained in step (2) under heating at 75° C. in a water bath for 10-50 minutes, and then immediately cooling in an ice bath after removing;
(4) centrifuging the cooled mixed solution obtained in step (3) at high speed under low temperature with the supernatant discarded;
(5) washing the pellets obtained in step (4) by centrifuging with distilled water for three times to obtain another pellets as ferrihydrite nanoparticles.

The preferred ratio of PEG to $Fe^{3+}$ in step (2) is 1:5-1:30;
The further preferred ratio of PEG to $Fe^{3+}$ in step (2) is 1:20.

Preferably stirring for 20 minutes under heating in a water bath in step (3).

The second aspect of the present invention provides a ferrihydrite nano-photosensitizer synthesized by above method, the ferrihydrite nano-photosensitizer is in a highly dispersed state and has a particle size of 20-30 nm.

The third aspect of the present invention provides a use of the ferrihydrite nano-photosensitizer synthesized by above method in preparing an antibacterial drug and an anticancer drug.

The beneficial effects of the present invention are:
(1) In the present invention, PEG is added in the process of $Fe^{3+}$ hydrolysis and nucleation, so that, on the one hand, further aggregation of ferrihydrite after nucleation can be avoided, and the highly dispersed PEG-Fns with a particle size of 20-30 nm is obtained; on the other hand, PEG-Fns can be effectively absorbed by cells due to its high biocompatibility after being modified by PEG.

(2) The PEG-Fns synthesized in the present invention can adsorb microorganisms due to retaining the adsorption property of the ferrihydrite itself, and has a high sensitivity and specificity to ordinary blue light.

(3) The PEG-Fns synthesized in the present invention can be controllably induced and reduced by blue light to release $Fe^{2+}$, the released $Fe^{2+}$ can convert $H_2O_2$ into •OH through Fenton reaction in the cell, which induces cell oxidative damage and destroys microbial cell membrane, thereby achieving anticancer and antibacterial purposes.

(4) The PEG-Fns synthesized in the present invention has antibacterial capacity at pH from 3.6 to 7.4, and thus has a wide range of uses.

(5) The synthesis method adopted by the invention has the advantages of low synthesis cost, simple operation steps, easy control of reaction conditions, and rapid preparation of large quantities.

DETAILED DESCRIPTION OF EMBODIMENTS

In order to understand the above objective, features and advantages of the present invention more clearly, the present invention will be described in detail below with reference to the accompanying drawings and specific embodiments. It should be noted that the embodiments of the application and the features in the embodiments can be combined with each other if there is no conflict.

Unless defined otherwise, all technical and scientific terms used herein have the same meaning as commonly understood by those skilled in the technical field of the present invention. The terms used in the description of the present invention herein are only for the purpose of describing specific embodiments, and are not intended to limit the present invention.

Embodiment 1

Figure 1:
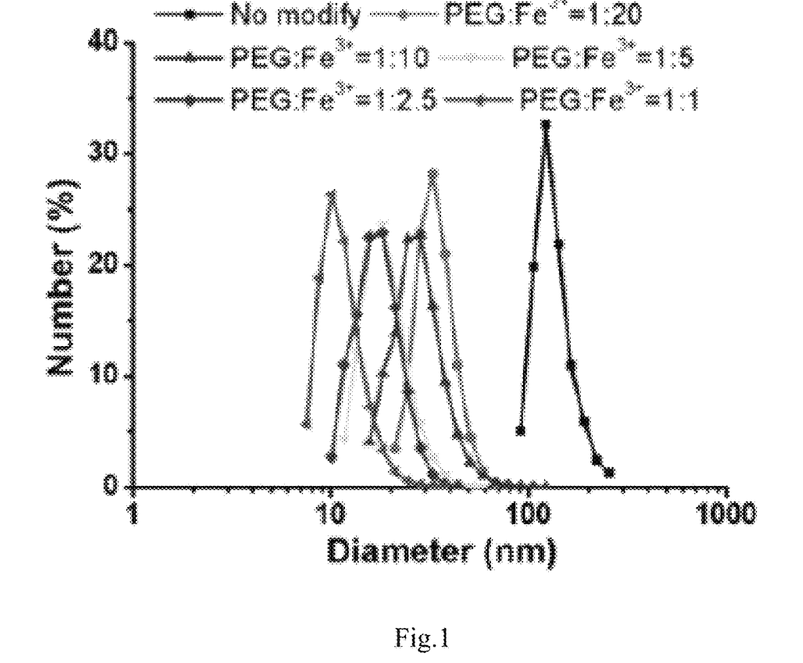
FIG. 1 shows the particle size of PEG-Fns obtained with different PEG modification ratios.

A method for synthesizing a new ferrihydrite nano-photosensitizer, comprising steps of:

weighing 303 mg of $Fe(NO_3)_3 \cdot 9H_2O$ solid dissolved fully in 30 ml of distilled water to prepare a 0.75 mM of $Fe(NO_3)_3$ solution in water; adding 125 mg of PEG solid to the solution in water by stirring to fully dissolve at a ratio of PEG to $Fe^{3+}$ of 1:1, 1:2.5, 1:5, 1:10, respectively; stirring the obtained solution under heating at 75° C. in a water bath for 10 minutes, and then immediately cooling in an ice bath after removing; centrifuging the cooled mixed solution at high speed under low temperature with the supernatant discarded, and then washing the obtained pellets with distilled water for three times. The obtained pellets were the ferrihydrite nanoparticles with a particle size less than 50 nm. The particle size of PEG-Fns was shown in FIG. 1.

Embodiment 2

Figure 2:
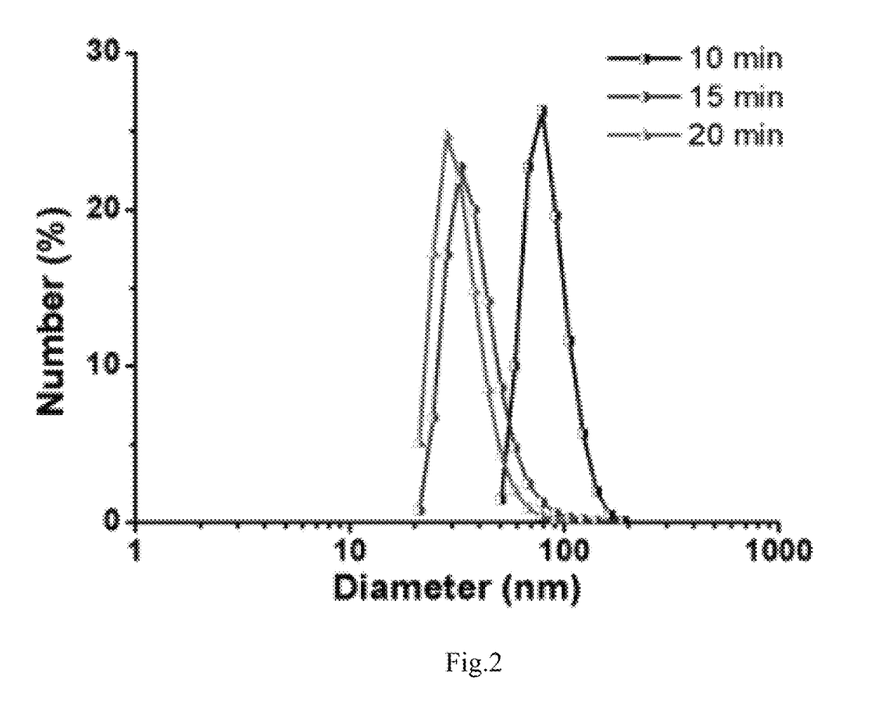
FIG. 2 shows the particle size of PEG-Fns obtained by heating for different time when the PEG modification ratio is PEG:$Fe^{3+}$=1:20.
Figure 3:
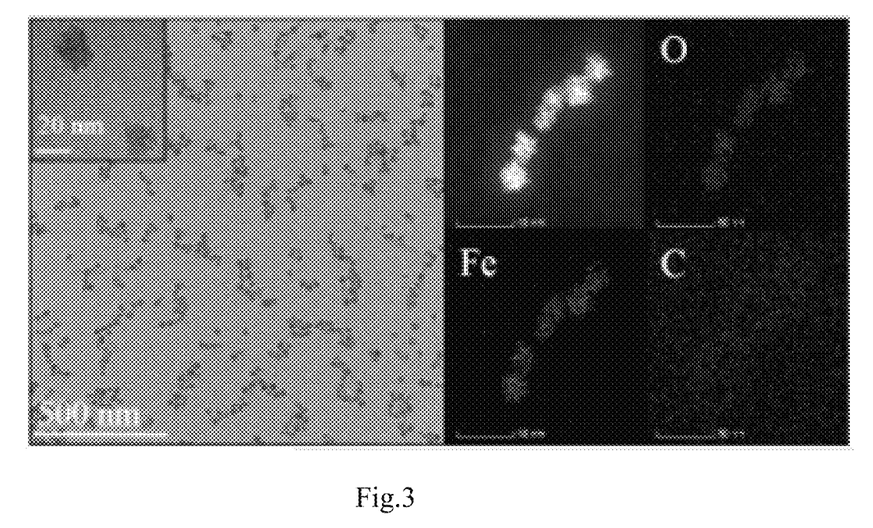
FIG. 3 shows electron micrograph and energy spectrum results of the synthesized PEG-Fns when the optimal conditions of PEG:$Fe^{3+}$=1:20 and heating for 20 minutes are selected.
Figure 4:
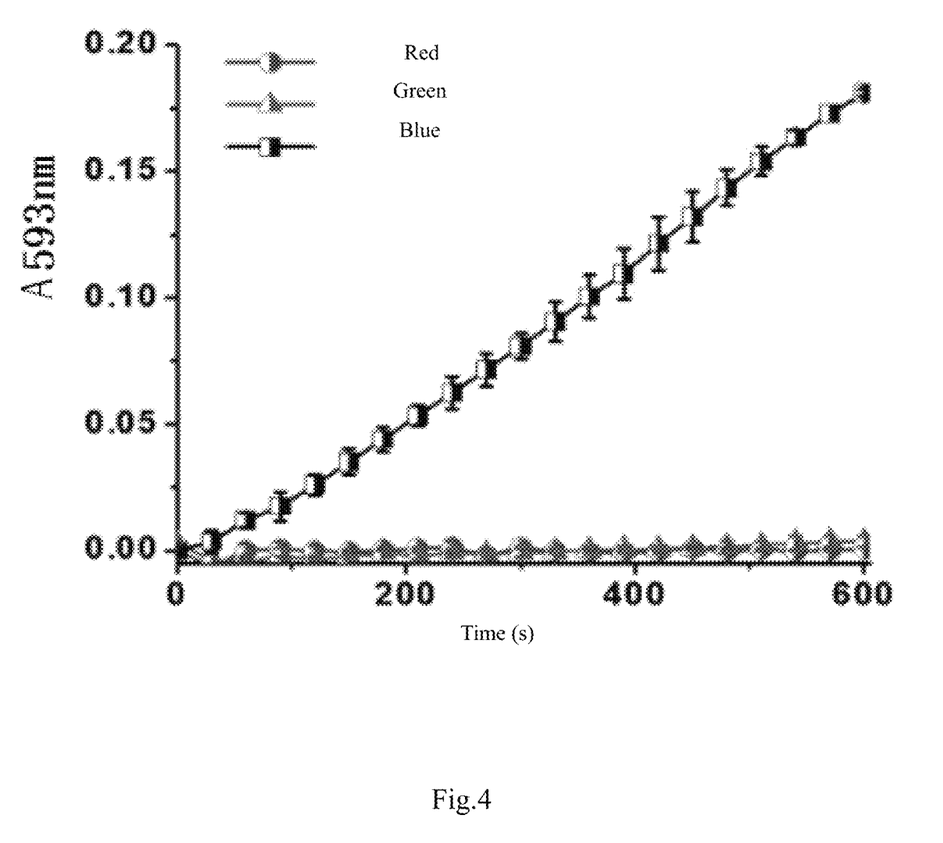
FIG. 4 shows that the synthesized PEG-Fns is specifically induced to release $Fe^{2+}$ by blue light when the optimal conditions of PEG:$Fe^{3+}$=1:20 and heating for 20 minutes are selected.
Figure 5:
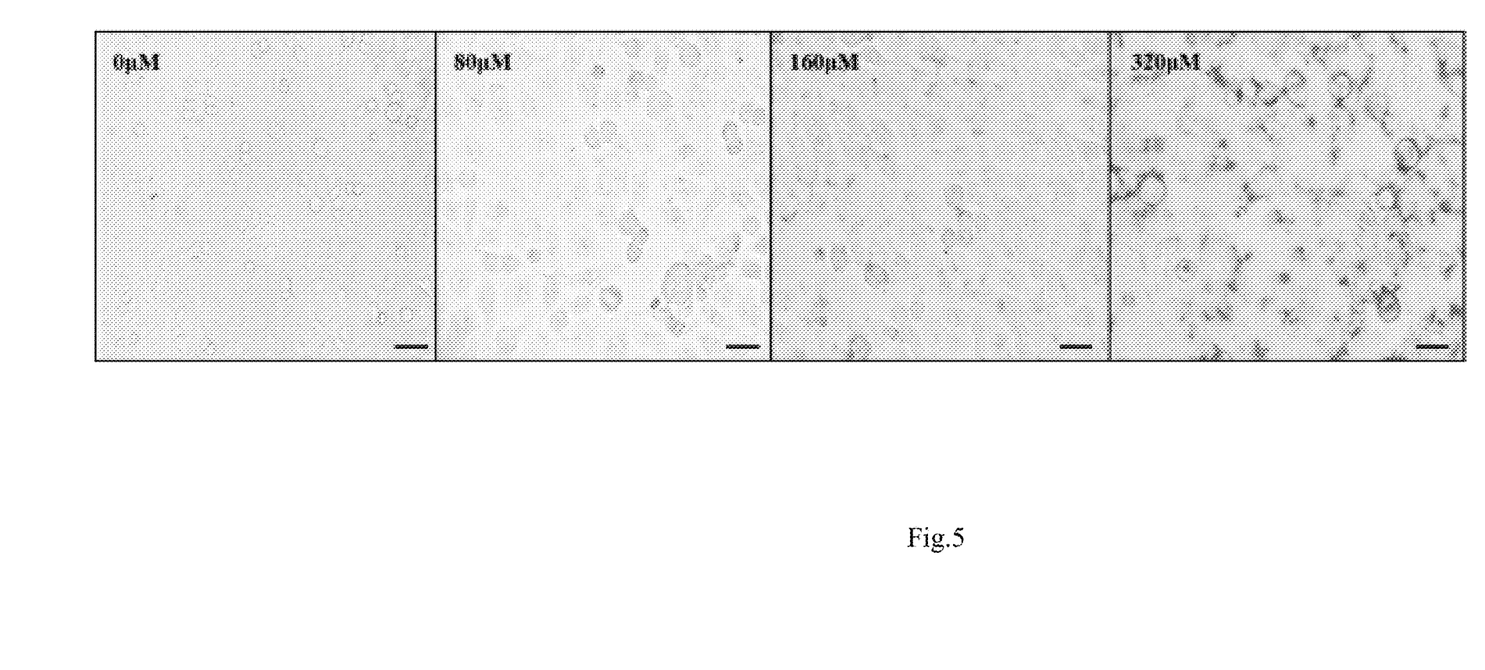
FIG. 5 shows that when PEG-Fns synthesized under optimal conditions are incubated with cells at different concentrations, they can be effectively absorbed by cells in the mouse tumor cell proliferation inhibition experiment in vitro (scale bar: 50 μm)

A method for synthesizing a new ferrihydrite nano-photosensitizer, comprising steps of:

weighing 303 mg of $Fe(NO_3)_3 \cdot 9H_2O$ solid dissolved fully in 30 ml of distilled water to prepare a 0.75 mM of $Fe(NO_3)_3$ solution in water; adding 125 mg of PEG solid to the solution in water by stirring to fully dissolve at a molar ratio of PEG to $Fe^{3+}$ of 1:20; stirring the obtained solution under heating at 75° C. in a water bath for 10 minutes, and then immediately cooling in an ice bath after removing; centrifuging the cooled mixed solution at high speed under low temperature with the supernatant discarded, and then washing the obtained pellets with distilled water for three times. The obtained pellets was the ferrihydrite nanoparticles with a particle size d≈100 nm. The particle size of PEG-Fns was shown in FIG. 2.

Embodiment 3

A method for synthesizing a new ferrihydrite nano-photosensitizer, comprising steps of:

weighing 303 mg of $Fe(NO_3)_3 \cdot 9H_2O$ solid dissolved fully in 30 ml of distilled water to prepare a 0.75 mM of $Fe(NO_3)_3$ solution in water; adding 125 mg of PEG solid to the solution in water by stirring to fully dissolve at a molar ratio of PEG to $Fe^{3+}$ of 1:20; stirring the obtained solution under heating at 75° C. in a water bath for 15 minutes, and then immediately cooling in an ice bath after removing; centrifuging the cooled mixed solution at high speed under low temperature with the supernatant discarded, and then washing the obtained pellets with distilled water for three times. The obtained pellets were the ferrihydrite nanoparticles with a particle size (d) about 30 nm, some of which have a larger particle size d≈100 nm. The particle size of PEG-Fns was shown in FIG. 2.

Embodiment 4

A method for synthesizing a new ferrihydrite nano-photosensitizer, comprising steps of:

weighing 303 mg of $Fe(NO_3)_3 \cdot 9H_2O$ solid dissolved fully in 30 ml of distilled water to prepare a 0.75 mM of $Fe(NO_3)_3$ solution in water; adding 125 mg of PEG solid to the solution in water by stirring to fully dissolve at a molar ratio of PEG to $Fe^{3+}$ of 1:20; stirring the obtained solution under heating at 75° C. in a water bath for 20 minutes, and then immediately cooling in an ice bath after removing; centrifuging the cooled mixed solution at high speed under low temperature with the supernatant discarded, and then washing the obtained pellets with distilled water for three times. The obtained pellets were the ferrihydrite nanoparticles with d≈20 nm; thus the condition of PEG:$Fe^{3+}$=1:20 and heating for 20 minutes selected in this embodiment was optimal. The particle size of PEG-Fns was shown in FIG. 2.

Embodiment 5

A method for synthesizing a new ferrihydrite nano-photosensitizer, comprising steps of:

weighing 303 mg of $Fe(NO_3)_3 \cdot 9H_2O$ solid dissolved fully in 30 ml of distilled water to prepare a 0.75 mM of $Fe(NO_3)_3$ solution in water; adding 125 mg of PEG solid to the solution in water by stirring to fully dissolve at a molar ratio of PEG to $Fe^{3+}$ of 1:50; stirring the obtained solution under heating at 75° C. in a water bath for 20 minutes, and then immediately cooling in an ice bath after removing; centrifuging the cooled mixed solution at high speed under low temperature with the supernatant discarded, and then washing the obtained pellets with distilled water for three times. The obtained pellets were the ferrihydrite nanoparticles.

The experimental effect evaluation of the ferrihydrite nano photosensitizer obtained in the above Embodiment 4

1. Mouse Tumor Cell Proliferation Inhibition Experiment In Vitro

The cells used in this experiment were SCC-7 cells, which were mouse squamous epidermal carcinoma cells.

The cells grown in the logarithmic phase were seeded in a 96-well plate at a density of $1\times10^4$/well, and adhered overnight in a cell incubator at 37° C. and 5% $CO_2$. The cells were incubated with PEG-Fns diluted with culture medium to concentrations of 0 μM, 80 μM, 160 μM, and 320 μM (using the amount of $Fe^{3+}$ in PEG-Fns as the concentration unit) for 12 hours, with three replicates for each concentration. Thereafter, the medium was replaced with phenol red-free medium, stimulated with blue light for 30 minutes. The H2DCFDA probe was used to detect the level of ROS in the cells, while continuing to incubate with cells at different times, and the CCK-8 kit was used to detect changes in cells activity; the cells grown in the logarithmic phase were seeded in a confocol cell culture dish, and then the cells were treated with the above method. The cell survival around light source was observed by confocal microscopy (Leica TCS SP8) after double-stained with Calcein-AM/PI.

Figure 6:
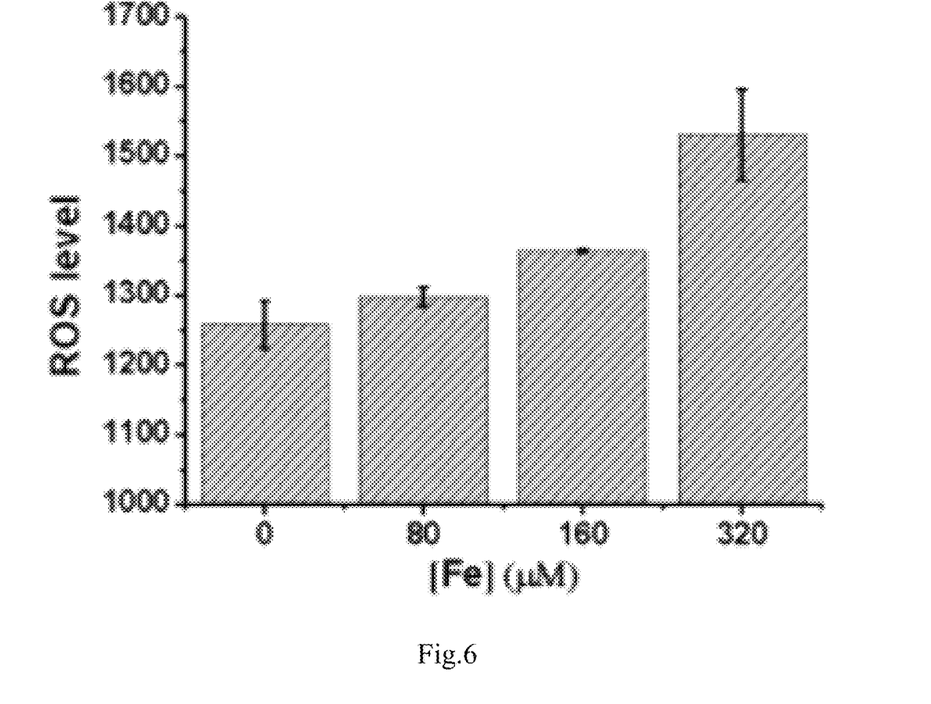
FIG. 6 shows changes of intracellular ROS level in the mouse tumor cell proliferation inhibition experiment in vitro.
Figure 7:
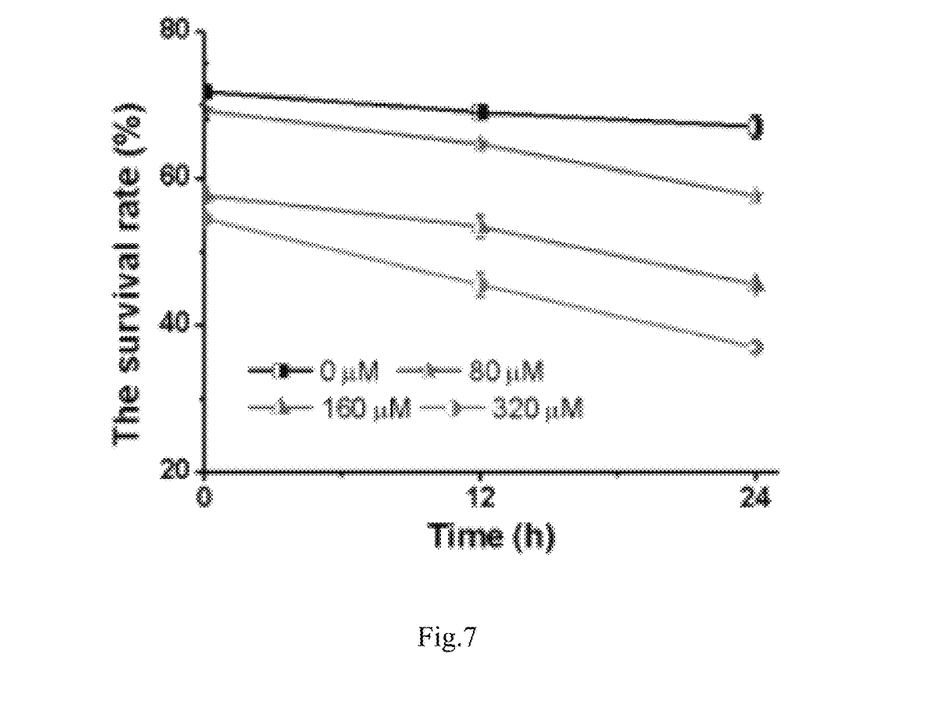
FIG. 7 shows changes of cell viability during the continued incubation in the mouse tumor cell proliferation inhibition experiment in vitro.
Figure 8:
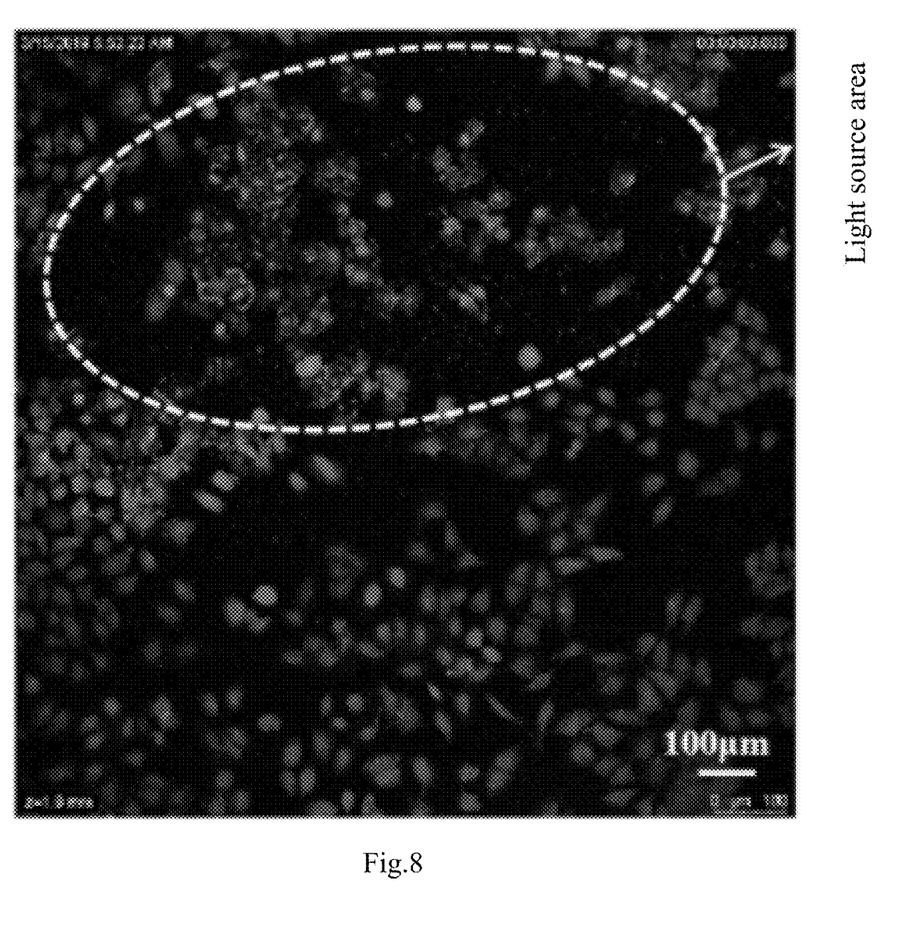
FIG. 8 shows the damage of cells around light source during the continued incubation in the mouse tumor cell proliferation inhibition experiment in vitro.

As shown in FIGS. 6, 7 and 8, when the final concentration of PEG-Fns reached 320 μM, the intracellular ROS level caused by the blue light system increased by about 30% compared with the group without PEG-Fns. After 24 hours, the cell viability dropped to 30%, and continued to decline, and approached 100% cell killing rate. Such killing did not extend to areas outside the light source, indicating that PEG-Fns itself was non-toxic to cells.

2. Antitumor Experiment In Vivo

Twelve healthy female Balb/c mice, SPF grade, inoculated with tumor cells at an amount of $5\times10^4$ after shaving their hair in the groin. Treatment was started until achieving the tumor diameter d=5 mm (10 days): 3 mice/group, animals were randomly divided into PEG-Fns treatment group (intratumoral injection of 5 μmol PEG-Fns/mouse), blue light treatment group (blue light stimulation at tumor site 30 minutes), PEG-Fns+blue light treatment group (intratumor injection of 5 μmol PEG-Fns/mouse, blue light stimulation at tumor site for 30 minutes after 48 hours), and control group (intratumoral injection of the same amount of saline).

Figure 9:
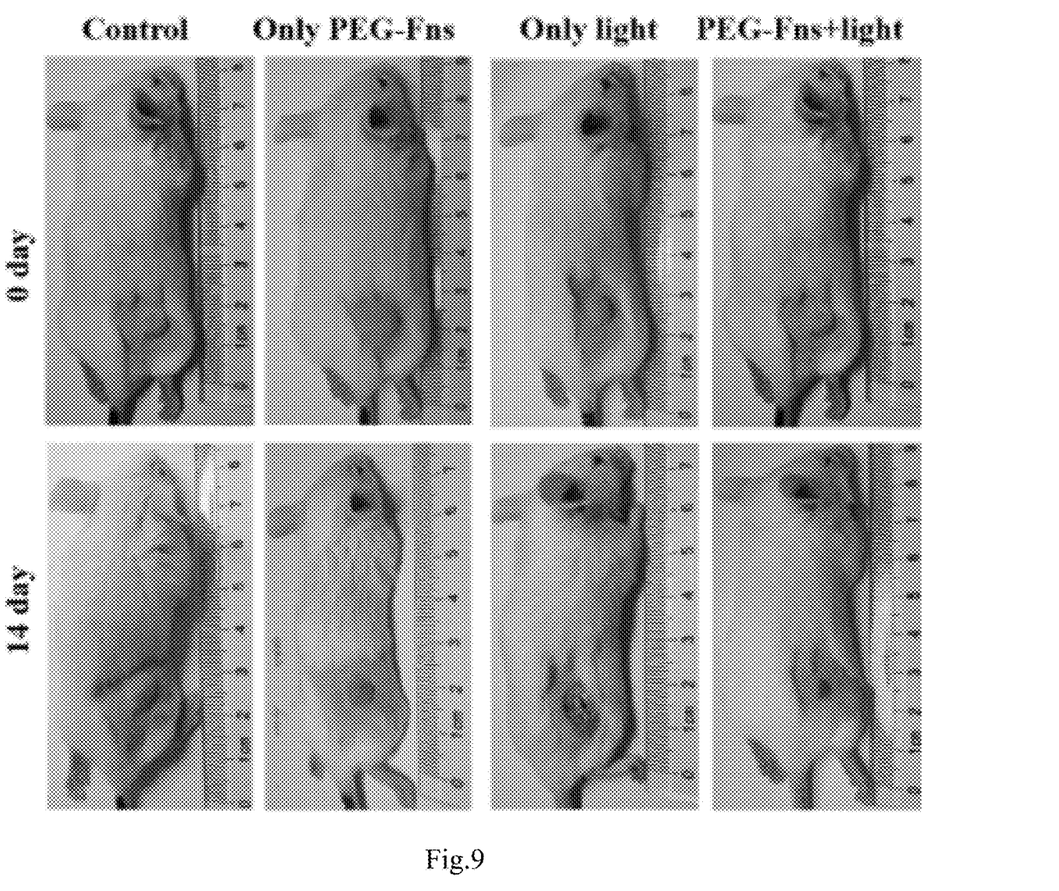
FIG. 9 shows the tumor recovery of mice in each group after treatment in the antitumor experiment in vivo.
Figure 10:
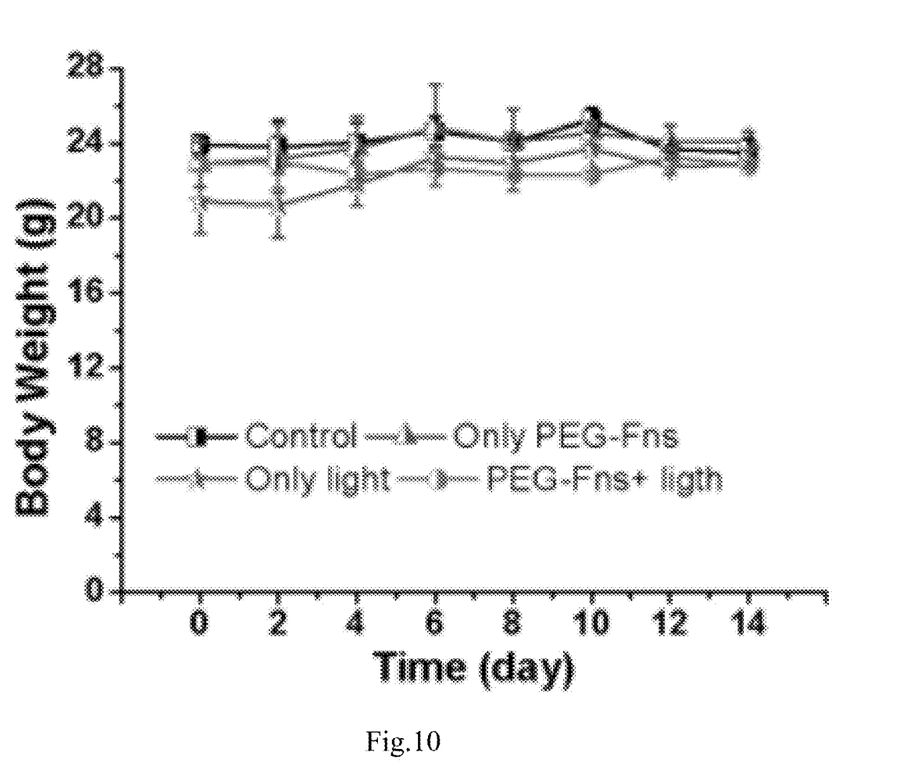
FIG. 10 shows weight changes of mice in each group during treatment in the antitumor experiment in vivo.

As shown in FIGS. 9 and 10, the tumors of the mice in the PEG-Fns+blue light treatment group were obviously scabs after 7 days, and they were substantially cured after 14 days, and the weight of the mice stabilized at about 24 g during the treatment, and there was no significant difference between groups. It was illustrated that the synthesized PEG-Fns of the present invention could effectively kill tumors in mice in the blue light system.

3. Antibacterial Experiment 1

Candida albicans in the logarithmic growth phase were collected and diluted to $10^6$ CFU $mL^{-1}$ with modified YPD liquid medium, with adding 25 mL of bacterial solution (final concentration: PEG-Fns 400 μM, $H_2O_2$ 0.5 mM) to a 50 mL culture flask which was incubated under shanking in blue light at 30° C. for 5 hours. 1 mL of bacterial solution was centrifuged at 4000 rpm for 3 minutes with removal 900 μL of supernatant, and the remaining 100 μL of supernatant was resuspended and coated on the sandcastle solid medium. After 12 hours, the antibacterial effect was analyzed.

Figure 11:
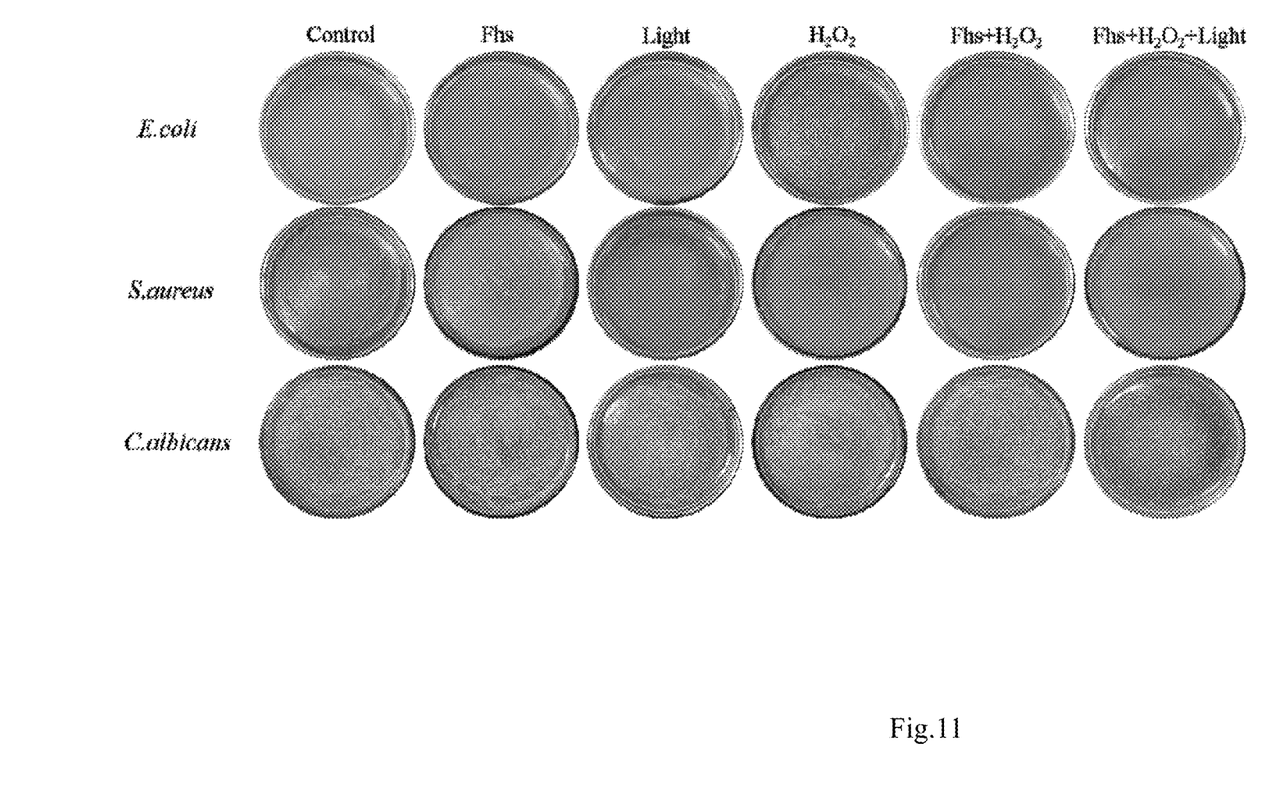
FIG. 11 shows the number of clones of fungi and bacteria with different treatments in the antibacterial experiment.

As shown in FIG. 11, PEG-Fns+$H_2O_2$+Light could significantly kill bacteria and fungi, and the lethality to bacteria and fungi was greater than 90%, indicating that PEG-Fns had strong antifungal and bacteria capacity.

4. Antibacterial Experiment II

*Escherichia coli* or *Staphylococcus aureus* in logarithmic growth phase were collected and diluted to $10^6$ CFU $mL^{-1}$ with LB liquid medium (1% peptone, 0.5% yeast powder, 1% NaCl, pH 7.0). Sterile cover slips with a diameter of 10 mm were placed in a 24-well plate, which was added 1 mL of *E. coli* or *Staphylococcus aureus* diluent, incubating in an incubator at 37° C. for 48 hours, with exchanging the medium every 24 hours. After 48 hours, the medium was removed, and the coverslips were washed twice with 10 mM pH 7.0 PBS buffer. 1 mL of LB liquid medium containing PEG-Fns and $H_2O_2$ (final concentration: PEG-Fns 400 μM, $H_2O_2$ 100 mM) was added and continued to incubate for 12 hours in an incubator at 37° C. under blue light. After blue light treatment for 12 hours, it was washed twice with PBS buffer to remove free bacteria, stained with Acridine Orange (AO) staining solution at 37° C. for 30 minutes in the dark, and washed twice with PBS buffer. The antibacterial effect was analyzed by a confocal microscope (Leica TCS SP8).

Experimental results illustrated that the synthesized PEG-Fns of the present invention could significantly kill bacteria in the presence of blue light and $H_2O_2$, with a lethality rate close to 90%, indicating that PEG-Fns had strong antibacterial capacity.

*Candida albicans* in the logarithmic growth phase were collected and diluted to $10^6$ CFU $mL^{-1}$ with YPD liquid medium (1% yeast powder, 2% peptone, 2% glucose, pH 5.6), and sterile cover slips with a diameter of 10 mm were place in a 24-well plate. 1 mL of *Candida albicans* dilution was added into the 24-well plate, incubating in an incubator at 30° C. for 48 hours, with exchanging the medium every 24 hours. The medium was removed after 48 hours. The cover slips were washed twice with 10 mM pH 7.0 PBS buffer, adding 1 mL of modified YPD liquid medium (400 µM PEG-Fns, 100 mM $H_2O_2$) under blue light and continuing to incubate in an incubator at 30° C. for 12 hours. After blue light treatment for 12 hours, it was washed twice with PBS buffer to remove free bacteria, stained with AO staining solution at 30° C. for 30 minutes in the dark, and washed twice with PBS buffer. The antibacterial effect was analyzed by a confocal microscope (Leica TCS SP8).

Figure 12:
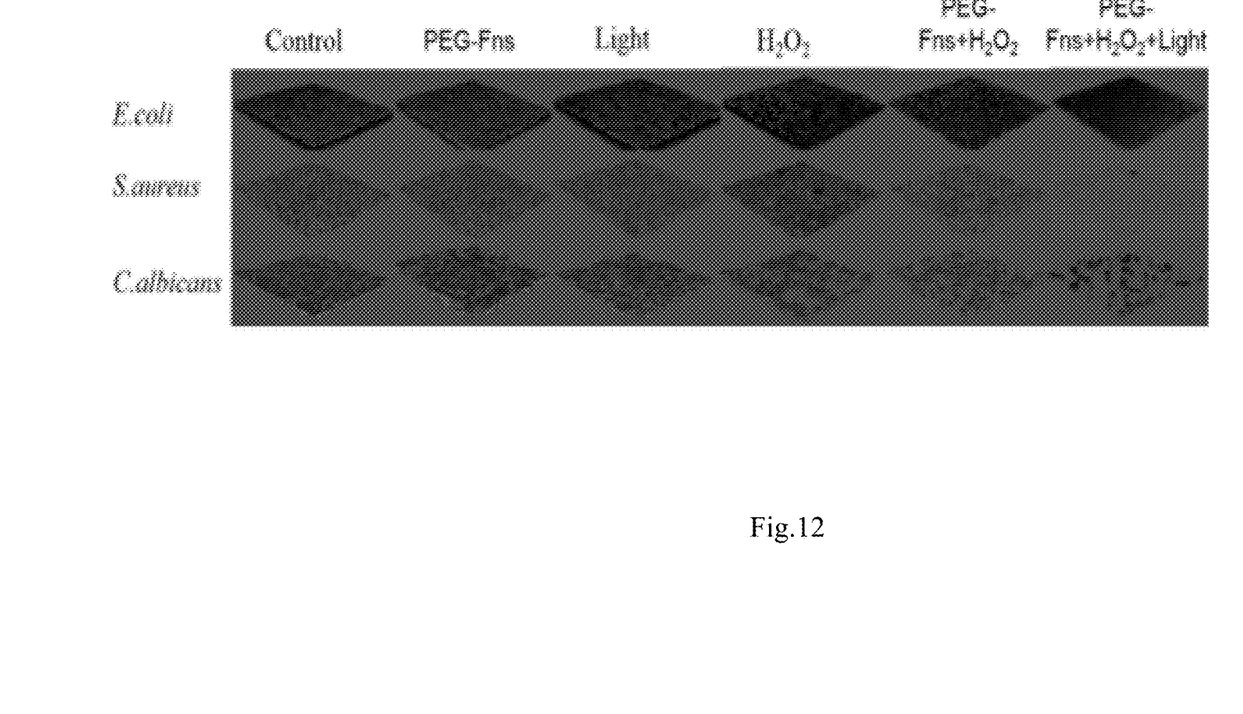
FIG. 12 shows the confocal microscope 3D images of biofilms composed of bacteria and fungi with different treatments in the antibacterial experiment.

As shown in FIG. 12, it could be seen from the 3D photo of the confocal microscope that the antibacterial effects of PEG-Fns, blue light, and $H_2O_2$ alone were not obvious, and the combination of these three factors could significantly kill the fungus with a lethality rate close to 90%, indicating that PEG-Fns had strong antifungal capacity.

Figure 13:
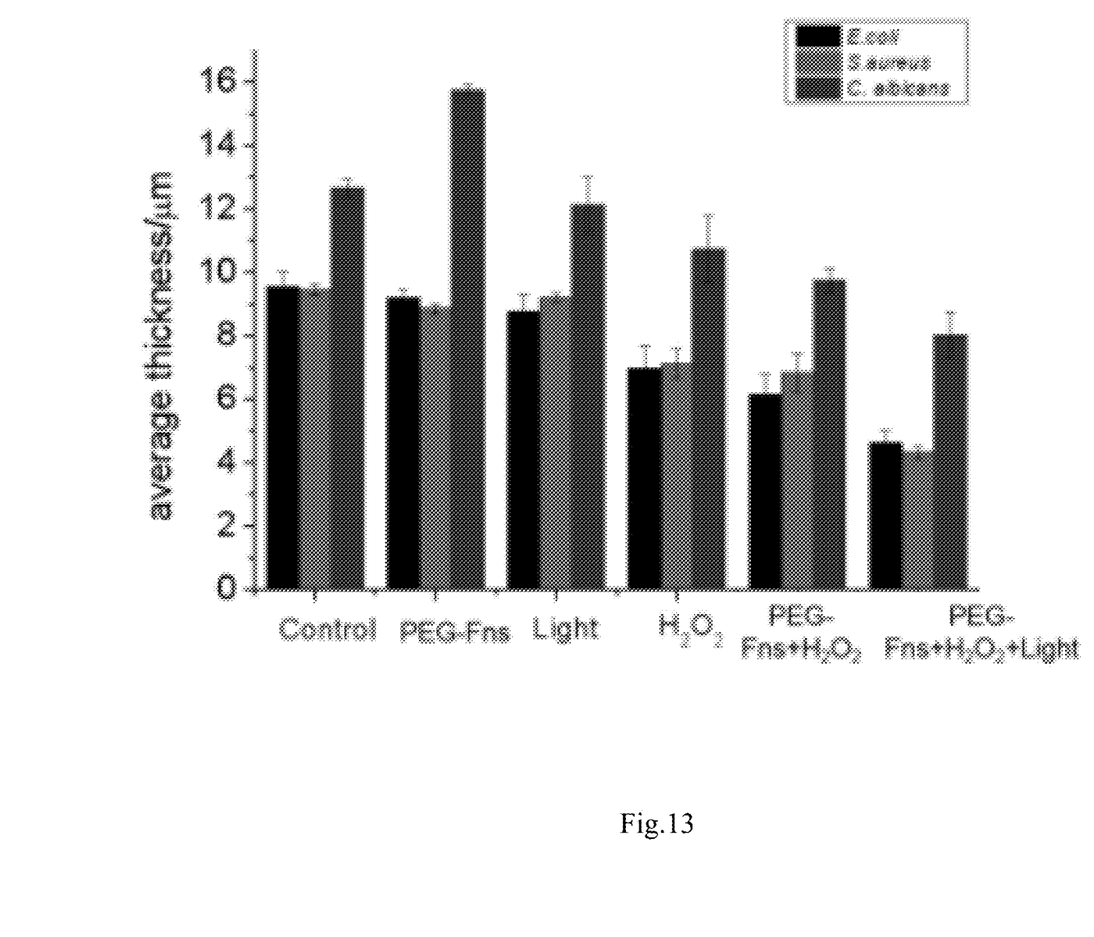
FIG. 13 shows the average thickness of biofilms composed of bacteria and fungi with different treatments in the antibacterial experiment.

As shown in FIG. 13, PEG-Fns treatment alone could promote the growth of bacteria and fungi from the average thickness of the biofilm composed of bacteria and fungi, furthermore, the treatment of blue light and $H_2O_2$ alone had no obvious effect on the growth of bacteria and fungi. However, compared with the control group, the PEG-Fns+$H_2O_2$+Light group could significantly kill bacteria and fungi. In summary, PEG-Fns could promote the killing of bacteria and fungi by $H_2O_2$ in the blue light system.

5. Wound Healing Experiment in Animals

Twenty-four Kunming mice aged 6-8 weeks were selected and divided into four groups, each with 6 mice. Animals were shaved on the would establishment and acclimated for a day. Two circular wounds with a diameter of 4 mm were established on the back of mice. The control groups were as follows: the wound without treatment; the wound treated with 20 µL of 700 µM PEG-Fns; the wound irradiated with blue light for 1 hour. In the experimental group, the wound was treated with 20 µL of 700 µM PEG-Fns and irradiated under blue light for 1 hour. Each group was treated once every 24 hours and photographed and recorded on days 0, 3, 7, and 11, respectively.

Figure 15:
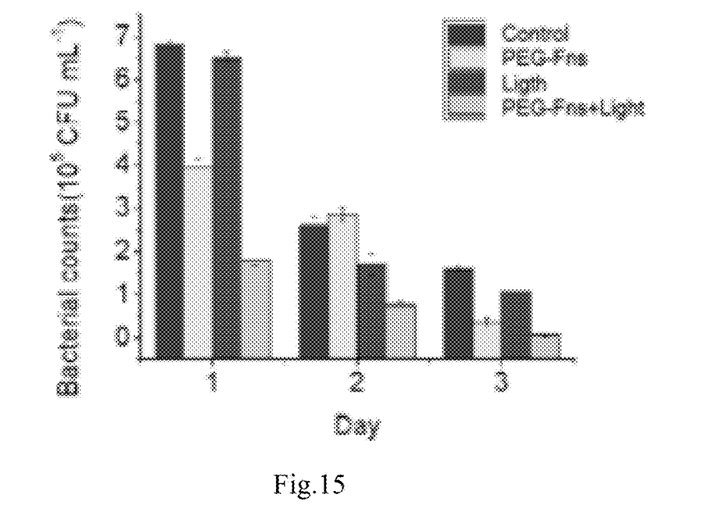
FIG. 15 shows the average number of bacterial and microbial clones in different groups of wounds in the first three days after treatment in the wound healing experiment in animals.

It could be seen from FIG. 15, the number of bacterial clones in the wound was significantly reduced in the experimental group compared with the control group. It could also be seen from the figure that PEG-Fns treatment alone could also reduce the number of bacterial clones in wounds, however, the colony of the clones was larger possibly due to adsorption effects of PEG-Fns, thus the true antibacterial effect of the PEG-Fns group alone could not be accurately measured.

Figure 14:
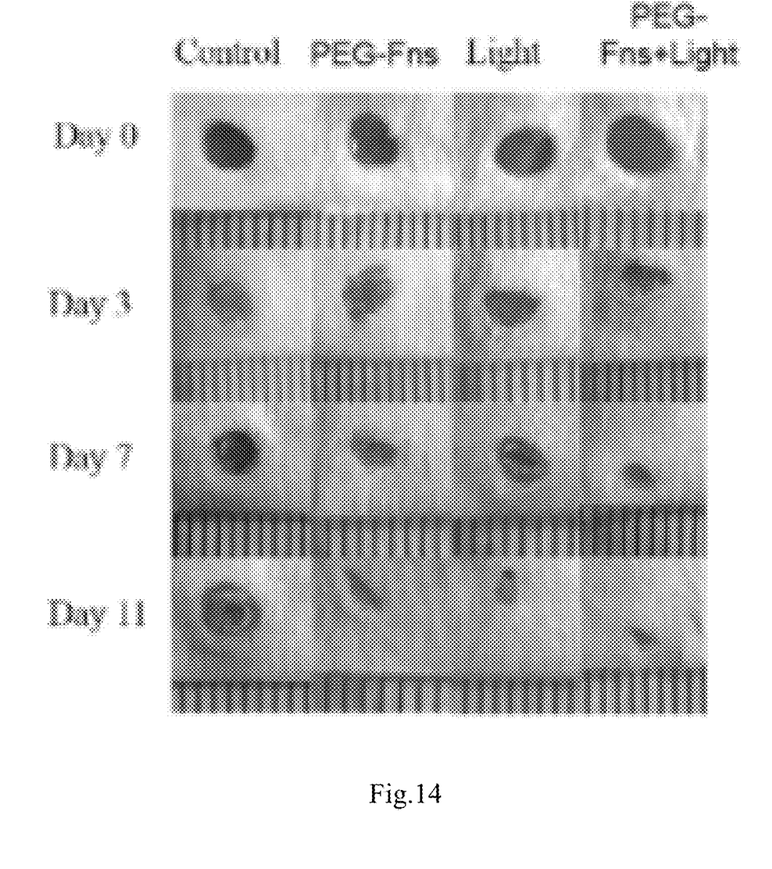
FIG. 14 shows images of wound areas of animals on days 0, 3, 7, and 11 in the wound healing experiment in vivo.
Figure 16:
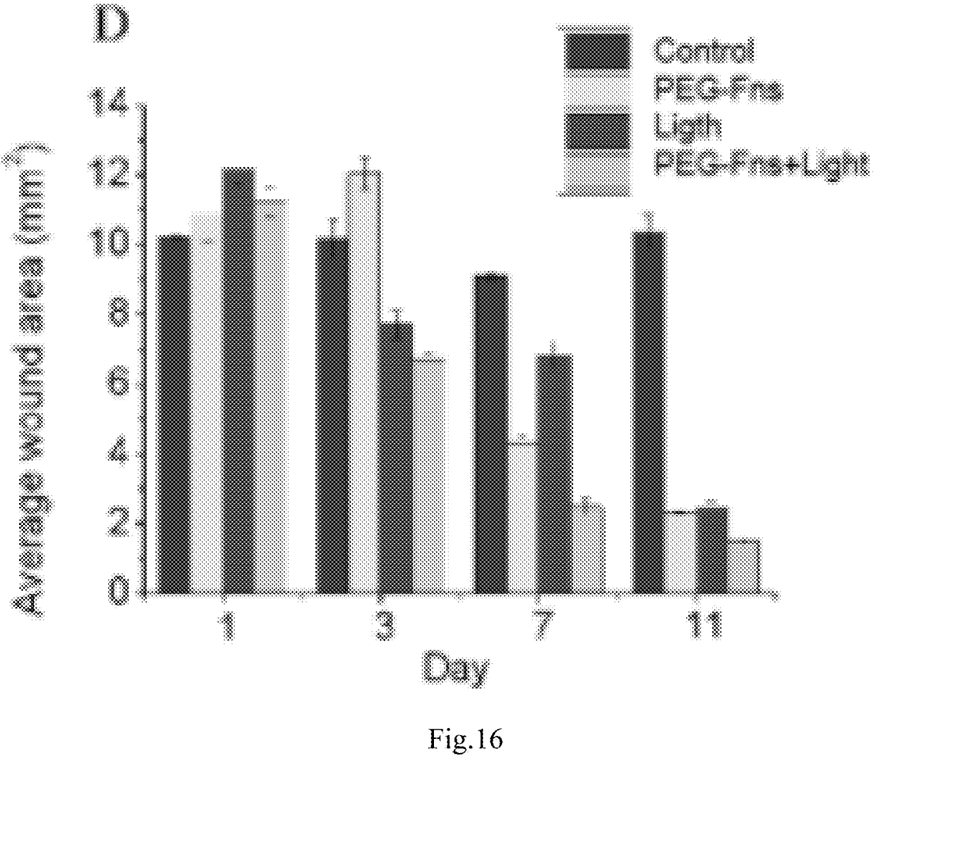
FIG. 16 shows the average wound area of different groups over time after treatment in the wound healing experiment in vivo.

It could be seen from FIGS. 14 and 16 that the wound areas of mice in the experimental group were significantly reduced compared with the control group on Day 7. Except for the control group, the wound areas of the other three groups were substantially healed on Day 11. We could also see from the figure that the PEG-Fns alone and blue light could also promote wound healing possibly due to promote the immune system. In summary, the $Fe^{2+}$ released by PEG-Fns irradiated with blue light could react with $H_2O_2$ produced from wounds in mice to inhibit the growth of wound bacteria and promote wound healing.

Finally, it should be noted that the above embodiments are only used to illustrate the technical solution of the present invention but not to limit them. Although the present invention has been described in detail with reference to the preferred embodiments, an ordinary person skilled in the art should understand that the technical solution of the present invention can be modified or equivalently replaced without departing from the spirit and scope of the technical solution of the present invention.

What is claimed is:

1. A method for synthesizing a new ferrihydrite nano-photosensitizer, comprising steps of:
   (1) weighing 303 mg of $Fe(NO_3)_3 \cdot 9H_2O$ solid dissolved fully in 30 ml of distilled water to prepare a 0.75 mM of $Fe(NO_3)_3$ solution in water;
   (2) adding PEG solid as a modifier to the solution in water obtained in step (1) by stirring to fully dissolve at a molar ratio of PEG to $Fe^{3+}$ of 1:1-1:50;
   (3) stirring the solution obtained in step (2) under heating at 75° C. in a water bath for 10-50 minutes, and then immediately cooling in an ice bath after removing;
   (4) centrifuging the cooled mixed solution obtained in step (3) at high speed under low temperature with the supernatant discarded to obtain pellets;
   (5) washing the pellets obtained in step (4) by centrifuging with distilled water for three times to obtain another pellets as PEG-modified ferrihydrite nanoparticles.

2. The method for synthesizing a new ferrihydrite nano-photosensitizer according to claim 1, wherein the molar ratio of PEG to $Fe^{3+}$ is 1:5-1:30.

3. The method for synthesizing a new ferrihydrite nano-photosensitizer according to claim 2, wherein the molar ratio of PEG to $Fe^{3+}$ is 1:20.

4. The method for synthesizing a new ferrihydrite nano-photosensitizer according to claim 1, wherein stirring for 20 minutes under heating in a water bath in step (3).

5. A ferrihydrite nano-photosensitizer synthesized by the method of claim 1, wherein the ferrihydrite nano-photosensitizer has a particle size of 20-30 nm.

6. A ferrihydrite nano-photosensitizer synthesized by the method of claim 1, wherein the ferrihydrite nano-photosensitizer is in a highly dispersed state.

* * * * *